United States Patent

Takatsuto et al.

Patent Number: 4,961,775
Date of Patent: Oct. 9, 1990

[54] BRASSINOSTEROID DERIVATIVES AND PLANT GROWTH REGULATORS

[75] Inventors: Suguru Takatsuto, Niigata; Hitoshi Sato; Fumio Futatsuya, both of Saitama, all of Japan

[73] Assignees: Nippon Kayaku Kabushiki Kaisha; Tama Biochemical Co., Ltd., both of Tokyo, Japan

[21] Appl. No.: 263,630

[22] Filed: Oct. 27, 1988

[30] Foreign Application Priority Data

Nov. 10, 1987 [JP] Japan .................. 62-282110

[51] Int. Cl.$^5$ .................. A01N 43/22; A01N 43/20
[52] U.S. Cl. .................. 71/88; 549/268
[58] Field of Search .................. 549/268; 71/88

[56] References Cited

FOREIGN PATENT DOCUMENTS 0040517 11/1981 European Pat. Off. ............ 549/268
0231088 12/1984 Japan .................. 549/268

OTHER PUBLICATIONS

Mori, "Synthesis of Brassinolide and Related Steroids with Plant Growth Promoting Activity", Latinoamer 16/2 55-59 (1985).
European Appln. No. 0 080 381 (Sumitomo).
J. Org. Chem., vol. 44, No. 26, 1979 pp. 5002-5004 "Synthesis of Brassino Steroids: New Plant-Growth-Promoting Steroids".
Agric. Biol. Chem., 48 (3), pp. 745-752, 1984 Short-Step Syntheses of Homodolicholide and Homodolichosterone.

Primary Examiner—Glennon H. Hollrah
Assistant Examiner—Amelia A. Owens
Attorney, Agent, or Firm—Henry C. Nields

[57] ABSTRACT

Disclosed herein is a novel brassinosteroid derivative represented by the formula:

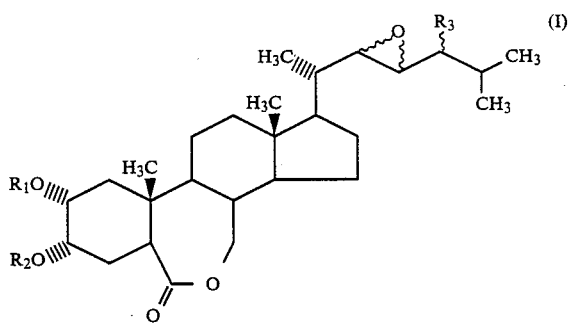

wherein
$R_3$ represents $C_{1-2}$-alkyl,
$R_1$ and $R_2$ which may be the same or different, represent hydrogen or acyl, respectively, otherwise $R_1$ and $R_2$, combining together, may form

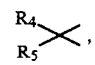

wherein
$R_4$ and $R_5$ represent $C_{1-2}$-alkyl, and $R_3$ represents methyl only in this case.

The brassinosteroid derivative represented by the above formula (I) exhibits a favorable plant growth regulating effect on various plants in agriculture and horticulture.

5 Claims, No Drawings

BRASSINOSTEROID DERIVATIVES AND PLANT GROWTH REGULATORS

BACKGROUND OF THE INVENTION:

The present invention relates to a novel brassinosteroid derivative, to a preparing process thereof, to a plant growth regulating composition comprising it, and to a method for regulating plant growth and leads to both quantitative improvements such as plant growth promotion and increasing yield, and qualitative improvements such as advance in quality and progress against stress in agriculture and horticulture Since brassinolide was discovered as a plant growth regulating substance in pollen of Brassica napa L. (M.D. Grove et al, Nature 281, p. 216, 1979), and epi-brassinolides by Thompson et al (J. Org. Chem., 44, p. 5002, 1979) was synthesized, numbers of brassinosteroids have been found in natural products, and novel derivatives by synthesis have been reported, which are described in detail in a recent review (Yukigoseikagaku, 43,p. 849, 1985).

It has been confirmed that brassinolide and its related compounds exhibit a growth regulating activity to plant, such as lamina joint inclination of rice plant, and various investigations have been continued in search of valuable industrial utilization. However, ever known brassinosteroids show so short-term effect on plants that they are unsuitable for demand to durable activity. Any brassinosteroids which would exhibit a durable effect on plant might be evaluated highly in industry, so that such brassinosteroids have been expected.

The present invention, a result of intensive investigations, has succeeded in finding the substance able to serve the purpose, and thus has been accomplished.

SUMMARY OF THE INVENTION:

In a first aspect of the present invention, there is provided A brassinosteroid derivative represented by the formula:

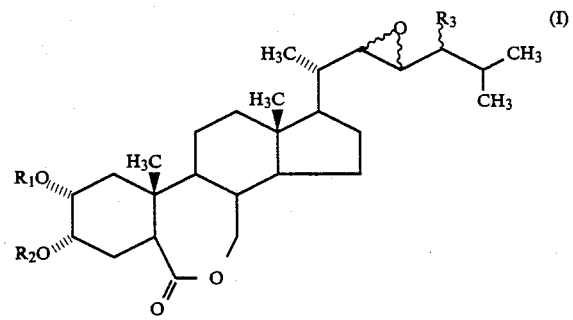

wherein R represents $C_{1-2}$-alkyl, $R_1$ and $R_2$ which may be the same or different, represent hydrogen or acyl, respectively, otherwise $R_1$ and $R_2$, combining together, may form

wherein $R_4$ and $R_5$ represent $C_{1-2}$-alkyl, and $R_3$ represents methyl only in this case.

In a second aspect of the present invention, there is provided a plant growth regulating composition comprising an effective amount of brassinosteroid represented by the

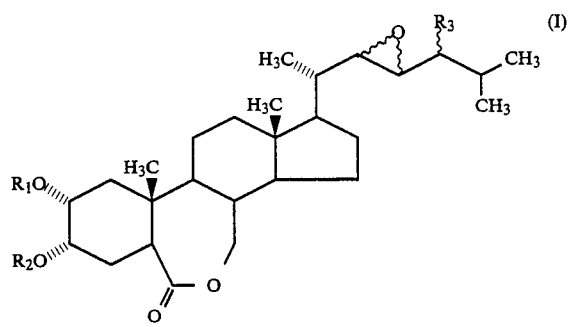

wherein $R_1$, $R_2$ and $R_3$ are as defined above, as the effective component.

In a third aspect of the present invention, there is provided a method for regulating plant growth which comprises applying effective amount of a compound of the formula:

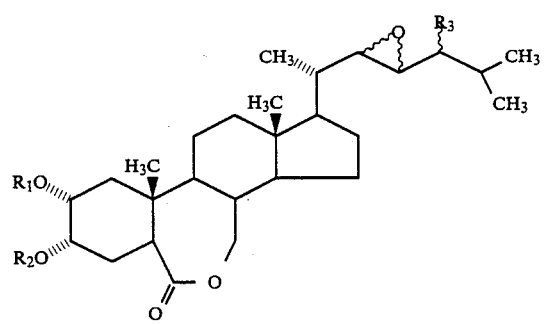

wherein $R_1$, $R_2$ and $R_3$ are as defined above.

In a fourth aspect of the present invention, there is provided a process for producing the brassinosteroids represented by the formula

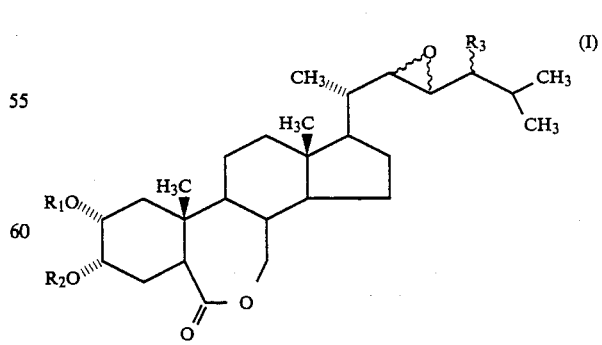

wherein $R_1$, $R_2$ and $R_3$ are as defined above, by oxidizing the compound represented by the formula:

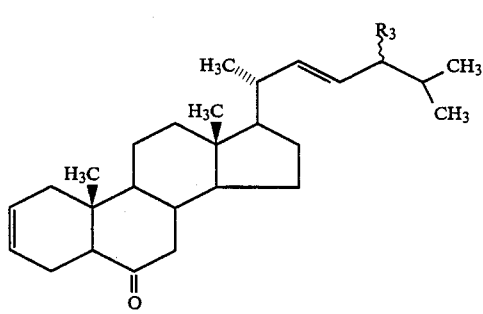

wherein $R_3$ is as defined above, to produce the derivative represented by the formula:

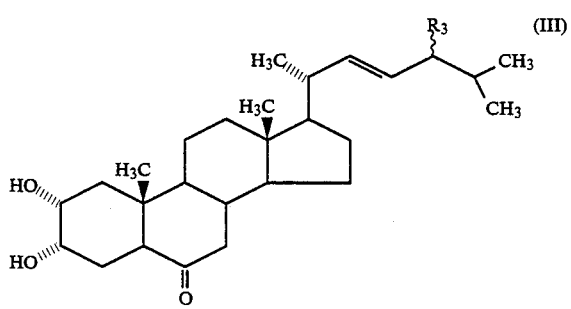

and oxidizing the derivative of the formula (III) or the derivative represented by the formula

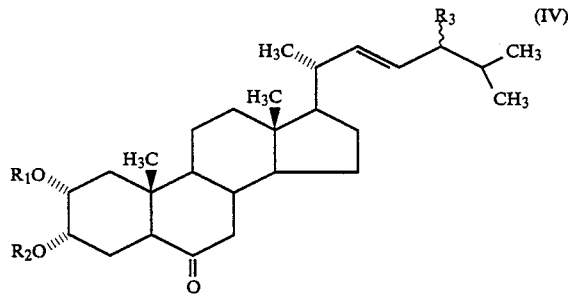

wherein $R_1$, $R_2$ and $R_3$ are as defined above with the proviso that neither of $R_1$ and $R_2$ are hydrogen, which is obtained by acylating the hydroxy groups of the derivative of the formula (III) or by converting the hydroxy groups of the derivative of the formula (III) to ketal.

DETAILED DESCRIPTION OF THE INVENTION:

The brassinosteroid derivative represented by the formula:

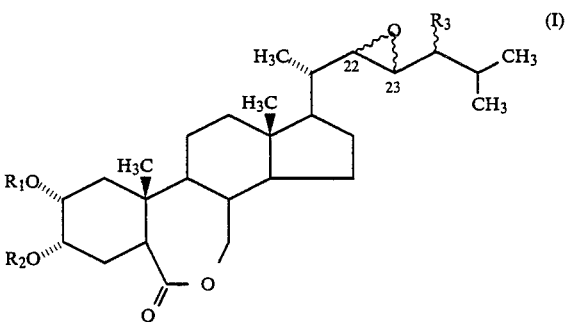

wherein $R_3$ represents $C_{1\text{-}2}$-alkyl, $R_1$ and $R_2$ which may be the same or different, represent hydrogen or acyl, respectively, otherwise $R_1$ and $R_2$, combining together, may form

wherein $R_4$ and $R_5$ represent $C_{1\text{-}2}$-alkyl, and $R_3$ represents methyl only in this case, has been invented as a novel brassinosteroid exhibiting high durability.

A brassinosteroid derivative of the formula (I) of the present invention can be prepared as described hereinafter. A compound represented by the formula:

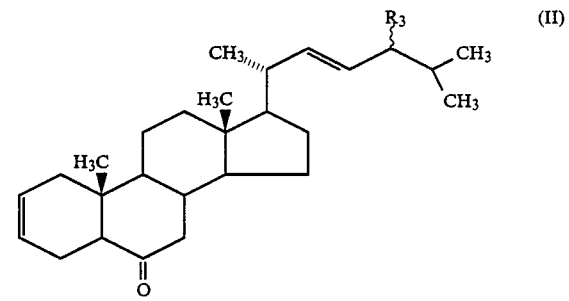

wherein $R_3$ represent $C_{1\text{-}2}$-alkyl, which can be obtained by the known method (Japanese Patent Laid-Open No. 161384/1981 and Yukigoseikagaku, 43, p. 849, 1985), may be oxidized by adding catalytic amount of osmium tetraoxide in the presence of an oxidizing agent such as a tertiary amine N-oxide, represented by N-methylmorpholine-N-oxide, if necessary, in a suitable solvent, preferably at 0° to 50° C., to produce a compound represented by the formula (III):

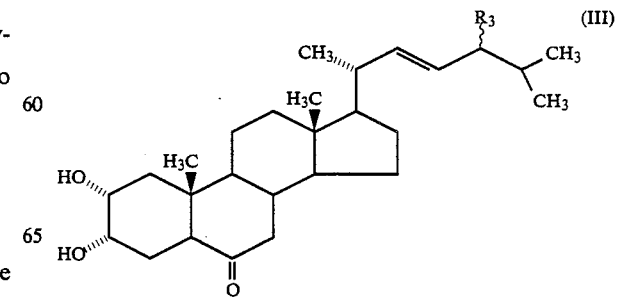

As the above suitable solvents, ethers such as diethyl ether, tetrahydrofuran and dioxane, halogenated hydrocarbons such as methylene chloride and chloroform, aromatic hydrocarbons such as benzene and toluene, alcohols such as isopropanol and t-butanol, esters such as ethyl acetate, water and solvent mixtures of arbitrary proportions of two or more kinds of those solvents, which may dissolve well the compound (II), are preferable. A process, wherein oxidizing agents such as t-butyl hydroperoxide are used (K.B. Sharples, J. Am. Chem. Soc., 98, 1986 (1976)), is favorable also besides the above. On conducting oxidation, controlling amount of the reagents for oxidation, and also checking progress of the reaction by means of thin layer chromatography, make it possible to hydroxylate selectively 2- and 3-positions in an excellent yield. Meanwhile, some stereo isomer at 2- and 3-positions which may be by-produced according to the reaction conditions, may be, if necessary, removed by recrystallization, or by means of column chromatography after the subsequent acylation. A compound represented by the formula (III) may be reacted with acylating agents such as acid anhydrides, for example, acetic anhydride and propionic anhydride, or acyl halides, for example, acetyl chloride and propionyl chloride, if necessary, in a suitable solvent, sometimes adding a suitable base, at 0° to 100° C., to give a compound represented by the formula (IV):

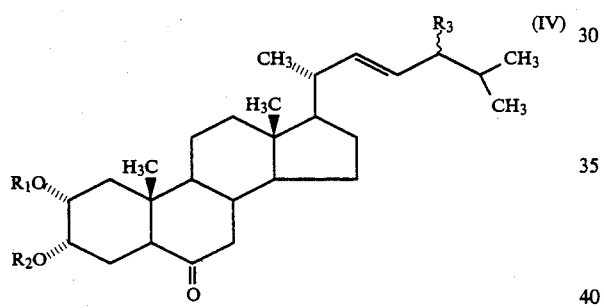

(IV)

wherein at least one of $R_1$ and $R_2$ is acyl and $R_3$ are as defined in the formula (I). The above suitable bases include inorganic bases such as sodium carbonate, potassium carbonate and sodium hydroxide, or organic bases such as trimethylamine, triethylamine, dimethylaniline, pyridine, 4-dimethylaminopyridine and priolines.

A compound represented by the formula:

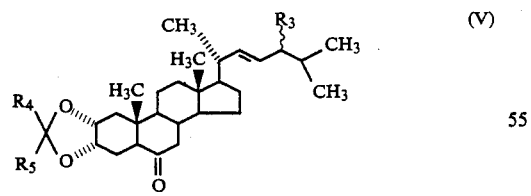

(V)

wherein $R_3$, $R_4$ and $R_5$ are as defined in the formula (I), may be obtained by reacting a compound represented by the formula (III) with ketones such as acetone, methyl ethyl ketone and diethyl ketone, or ketals such as and

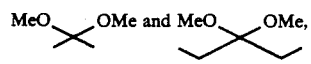

MeO⟩⟨OMe and MeO⟩⟨OMe, in the presence of a suitable acid catalyst, for example, p-toluenesulfonic acid, hydrochloric acid and sulfuric acid, in a high yield. As reaction solvents, the solvent used for production of a compound of the formula (IV) from a compound of the formula (III), or the above ketones or ketals used as the reactants, may be employed. Reaction temperature is preferably from 50° C. to boiling point of the solvent.

A compound of the formula (VI) or (VII) may be obtained by reacting a compound represented by the formula (III), (IV) or (V) with organic peracids such as trifluoroperacetic acid, monoperoxyphthalic acid and m-chloroperbenzoic acid, if necessary, in an organic solvent stable to oxidation. In that case, oxidation is conducted, preferably using m-chloroperbenzoic acid (m-CPBA) in solvents such as dichloromethane or perchloroethylene at a low temperature, preferably, −5° C. to room temperature.

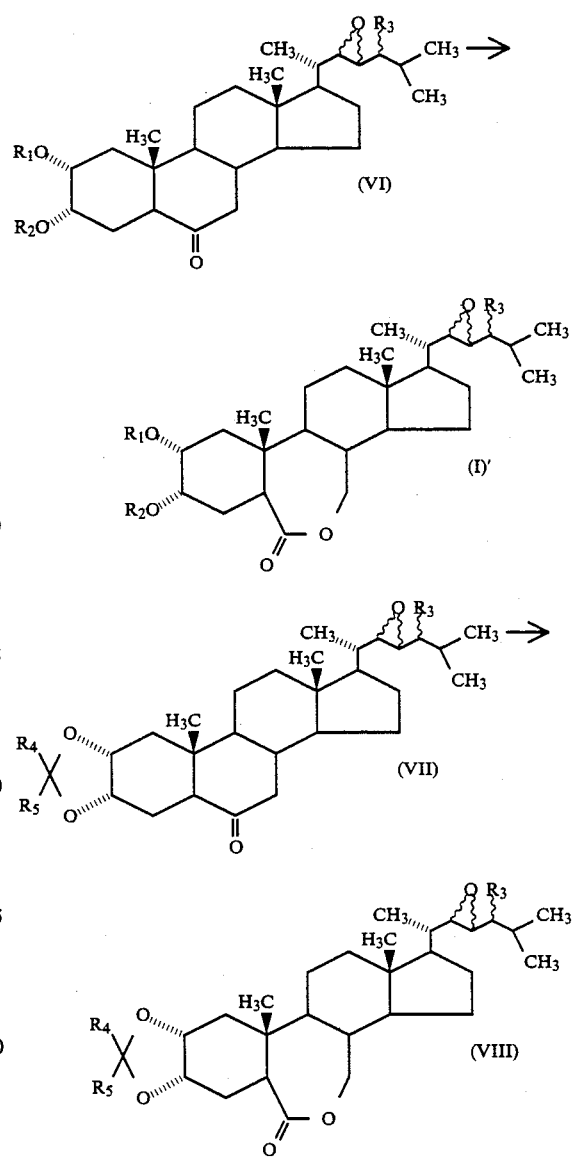

wherein $R_1$, $R_2$, $R_3$, $R_4$ and $R_5$ are as defined in the formula (I). A compound represented by the formula (VI) or (VII) is not isolated and continuously reacted, thus Baeyer-Villiger reaction may proceed to give a compound represented by the formula (I)' or (VIII). The obtained compound is a mixture of stereo isomers of the epoxide part, and may be isolated, if necessary, by means of column chromatography o recrystallization to give a compound represented by the formula (IX) and (X), wherein $R_1$, $R_2$ and $R_3$ are as defined in the formula (I), or a compound represented by the formula (XI) and (XII) wherein $R_3$, $R_4$ and $R_5$ are as defined in the formula (II).

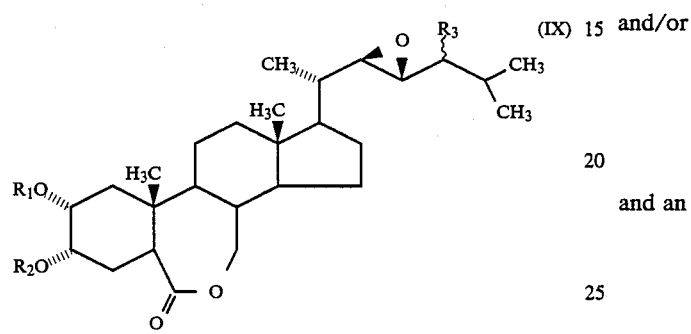
(IX)

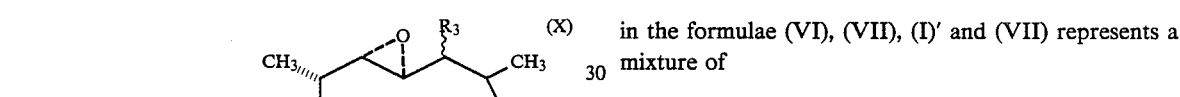
(X)

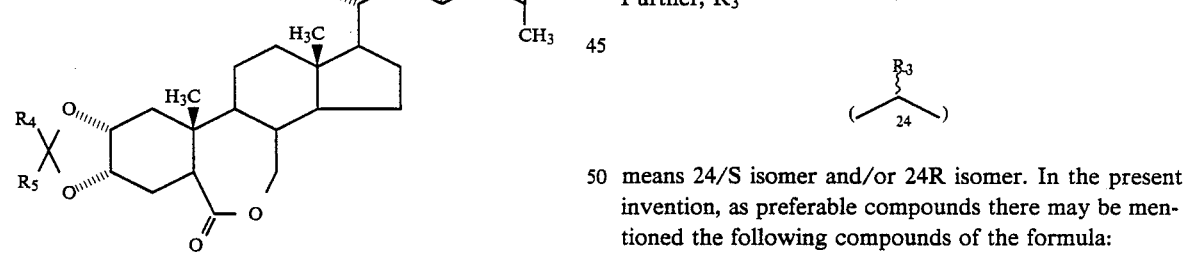
(XI)

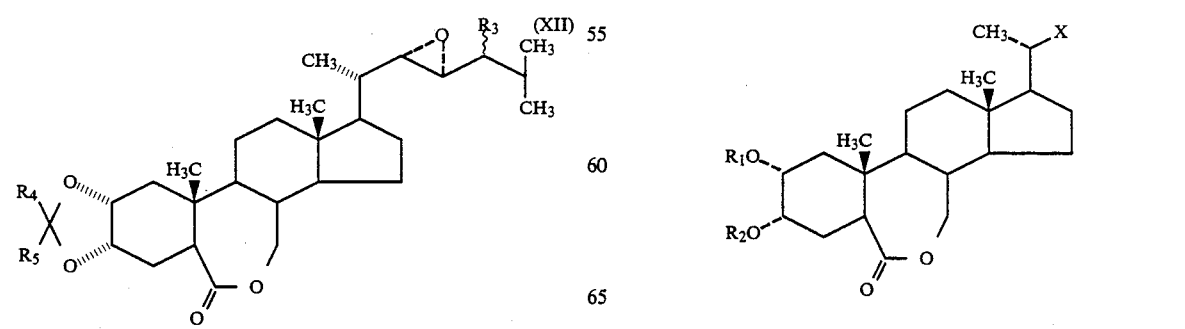
(XII)

Now, an exposy grop at 22, 23-position in the formula (I) of the present invention indicates

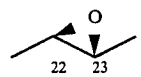

and/or

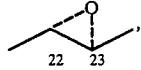, and an epoxy group

in the formulae (VI), (VII), (I)' and (VII) represents a mixture of

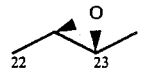

and

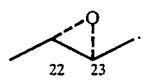.

Further, $R_3$

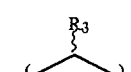

means 24/S isomer and/or 24R isomer. In the present invention, as preferable compounds there may be mentioned the following compounds of the formula:

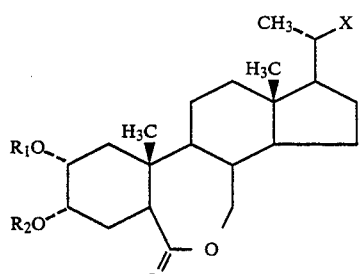

wherein $R_1$ and $R_2$ represent hydrogen or acetyl, X represents

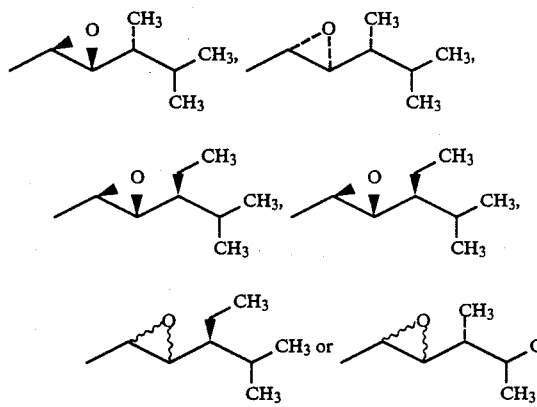
Examples of the compounds produced by the above process are illustrated in Tables 1 and 2, but the invention is not limited thereto.

TABLE 1-continued

[Structure shown with R₁O, R₂O, H₃C, CH₃, X substituents on steroid-like skeleton]

| Compound | R₁ | R₂ | X |
|---|---|---|---|
| No. 17 | " | " | epoxide-CH(CH₃)CH(CH₃)₂ |
| No. 18 | " | " | epoxide-CH(CH₃)CH(CH₃)₂ |
| No. 19 | " | " | epoxide-CH(CH₃)CH(CH₃)₂ |
| No. 20 | C₂H₅CO | C₂H₅CO | epoxide-CH(CH₃)CH(CH₃)₂ |
| No. 21 | " | " | epoxide-CH(CH₃)CH(CH₃)₂ |
| No. 22 | " | " | epoxide-CH(CH₃)CH(CH₃)₂ |
| No. 23 | CH₃CO | CH₃CO | epoxide-CH(CH₃)CH(CH₃)₂ |

TABLE 2

[Structure shown with R₄, R₅ forming dioxolane and X substituent on steroid-like skeleton]

| Compound | R₄ | R₅ | X |
|---|---|---|---|
| No. 24 | CH₃ | CH₃ | epoxide-CH(CH₃)CH(CH₃)₂ |
| No. 25 | " | " | epoxide-CH(CH₃)CH(CH₃)₂ |
| No. 26 | " | " | epoxide-CH(CH₃)CH(CH₃)₂ |
| No. 27 | " | " | epoxide-CH(CH₃)CH(CH₃)₂ |
| No. 28 | " | " | epoxide-CH(CH₃)CH(CH₃)₂ |
| No. 29 | CH₃ | CH₃ | epoxide-CH(CH₃)CH(CH₃)₂ |
| No. 30 | C₂H₅ | C₂H₅ | epoxide-CH(CH₃)CH(CH₃)₂ |

A novel compound represented by the formula (I) obtained in the above-mentioned manner exhibits a favorable effect on plants. When the compound is applied as a plant growth regulator, it can be used either alone or in the admixture of two or more of said compounds by dilution with water in low concentration, or it may be mixed with agrochemical adjuvants to make formulations such as dust, grain, tablet, solid drug, wettable powder, emulsion, and also liquids such as aqueous solution, dispersion and flowable solution. In this case, 0.001 to 10 parts of the derivative of the formula (I) may be used with 90 to 99,999 parts of an adjuvants to 100 parts of the total admixture.

Those adjuvants mentioned above include carriers (diluents) and other adjuvants such as spreaders, emulsifiers, wetting agents, dispersing agents, fixing agents and disintegrators.

As liquid carriers there can be mentioned aromatic hydrocarbons such as toluene and xylene, alcohols such as methanol, butanol and glycol, ketones such as acetone, amides such as dimethylformamide, sulfoxides such as dimethylsulfoxide, methylnaphthalene, cyclohexane, animal and vegetable oils, fatty acids and their esters, etc.

As solid carriers there are mentioned clay, kaolin, talc, diatomaceous earth, silica, calcium carbonate, montmorillonite, bentonite, feldspar, quartz, alumina, sawdust, etc.

As emulsifiers or dispersing agents, surfactants are generally used. They include anionic, cationic, nonionic and amphoteric surfactants such as sodium higher alkylsulfates, stearyltrimethylammonium chloride, polyoxyethylenealkylphenyl ether, lauryl betaine, etc.

In the case of use of those carriers, it is important to scrutinize carefully and employ those which are the most suitable for promoting the efficacy of the brassinolide derivatives.

A plant growth regulating composition of the present invention, prepared in the above various forms can be applied to plant bodies such as root, stem, leaf, flower, fruit and seed, or to soil for plant cultivation in the usual manner using suitable formulations.

In the present invention "apply" can include "spread", "spray", "sprinkle" or "soak".

The content of a novel brassinosteroid to be used as active ingredient in the composition of the present invention, may be determined appropriately according to the types of formulation, kinds of the plant to be applied, and the methods, times and periods of application, without any limitation, and when a brassinosteroid is formulated usually in an aqueous solution in measure, the concentration of the active ingredient is 0.0001 to 100 ppm, preferably 0.01 to 10 ppm, and the amount applied is generally 0.00001 to 100 mg/are, preferably 0.01 to 10 mg/are.

Any of said formulations of the present invention can be mixed, if necessary, with other plant growth regulators, and also with fertilizer components, herbicides, insecticides or pesticides.

The compound represented by the above formula (I) can be produced not only by a convenient process but also efficiently according to the present invention, and exhibits so favorable plant growth regulating effect on various plants in agriculture and horticulture that its utilization is highly valuable. For example, by treating plants in their seed or growth periods with the compound, growth promotion, disease tolerance, reduction of toxicity of herbicide, pesticide and insecticide, reduction of toxicity of salts, damage reduction against stress by low or high temperature and stress reduction to moisture are obtained successfully. It can improve yield and/or quality of graminaceous crops such as rice, wheat and corn, beans such as soy bean and bush bean, tubers such as potato and sweet potato and cruciferous crops such as rape, to apply a composition of the invention at about the time of flowering of said crops. Application of the composition to cucurbitaceae such as melon, sweet melon and cucumber and solanaceae such as tomato and egg-plant may increase their yield or improve their qualities such as taste and shape. No toxicity to plants is characteristic.

The present invention will be illustrated by following examples of practical preparation.

SYNTHESIS EXAMPLE 1

Synthesis of (22E,24R)-2α,3α-diacetoxy-5α-ergost-22-en-6-one:

(22E, 24R)-5α-Ergosta-2,22-dien-6-one (S. Takatsuto and N. Ikekawa, Chem. Pharm. Bull., 32, 2001 (1984)) (15.0 g, 37.9 mmol) was dissolved in a solvent mixture of tetrahydrofuran (100 ml) and water (10 ml), added with osmium tetraoxide (500 mg) and N-methyl-morpholine-N-oxide (15 g), and stirred at room temperature for 6 hours. Water (30 ml) and sodium hydrogen sulfite (1 g) were added thereto, and after stirring at room temperature for 30 minutes, extracted with dichloromethane. The obtained organic layer was washed with 2N hydrochloric acid and then with water, and dried over anhydrous magnesium sulfate. A product obtained by removal of solvents with an evaporator was dissolved in pyridine (100 ml), 50 ml of acetic anhydride was added thereto, and stirred at 60° C. overnight. After cooling, 100 ml of water was added thereto and left still for 30 minutes, then extracted with ethyl acetate. The obtained organic layer was washed with 2N hydrochloric acid, with saturated aqueous solution of sodium hydrogencarbonate and with saturated brine, successively, and dried over anhydrous magnesium sulfate, then solvents were removed by an evaporator to give a crude product. It was purified by means of silica-gel column chromatography to give (22E, 24R)-2α,3α-diacetoxy-5α-ergost-22-en-6-one (2.0 g, 12 %):

Rf 0.45 (benzene/ethyl acetate, 10:1), m.p. 196 to 197° C. (ethyl alcohol), and (22E, 24R)-2α,3α-diacetoxy-5α-ergost-22en-6-one (10.6 g, 64 %):

Rf 0.39 (benzene/ethyl acetate, 10:1), m.p. 210 to 212° C. (ethyl alcohol), $^1$H-NMR(CDCl$_3$) δ0.68 (3H, s, 18-H$_3$), 0.83 (3H, s, 19-H$_3$), 1.02 (3H, d, J=6.8 Hz, 21-H$_3$), 1.99 (3H, s, acetyl), 2.09 (3H, s, acetyl), 2.58 (1H, dd, J=10.3 and 6.4 Hz, 5α-H), 4.95 (1H, m, 2β-H), 5.18 (2H, m, 22-H and 23-H), 5.38 (1H, m, 3β-H), EI-MS m/s 514 (M$^+$)

SYNTHESIS EXAMPLE 2

Synthesis of (22R, 23R, 24R)-2α,3α-diacetoxy-22,23-epoxy-B-homo-7-oxa-5α-ergostan-6-one (1) and (22S, 23S, 24R)2α,3α-diacetoxy-22,23-epoxy-B-homo-7-oxa-5α-ergostan-6--one (2):

(22E, 24R)-2α,3α-diacetoxy-5α-ergost-22-en-6-one (5.33 q, 10.4 mmol) was dissolved in dichloromethane (60 ml), added with m-chloroperbenzoic acid (6.0 g, 34.8 mmol), and stirred in the dark at room temperature for 11 days. Powder of calcium hydroxide (6.0 g) and dichloromethane (100 ml) were added thereto, and after stirring at room temperature for 1 hour, the mixture was filtered and the solvent was removed with an evaporator to give a crude product. It was purified by means of silica-gel column chromatography (3.5 cmφ×34 cm) (benzene/ethyl acetate, 20:1+5:1) to give (22R, 23R, 24R)-2α,3α-diacetoxy-22,23-epoxy-B-homo-7-oxa-5α-ergostan-6-one (1) (0.87 g, 15%):

Rf 0.36 (benzene/ethyl acetate; 5:1), m.p. 213 to 215° C. (ethyl alcohol), $^1$H-NMR (CDCl$_3$) δ 0.67 (3H, s, 18-H$_3$), 0.98 (3H, s, 19-H$_3$), 1.99 (3H, s, acetyl), 2.13 (3H, s, acetyl), 2.71 (1H, m, 22-H), 3.00 (1H, dd, J=12 and 5 Hz, 5α-H), 4.09 (2H, m, 7-H2), 4.87 (1H, m, 2β-H), 5.36 (1H, m, 3β-H), FD-MS m/z 547 (M+¹), (22S, 23S, 24R)2α,3α-diacetoxy-22,23-epoxy-B-homo-7-oxa-5α-ergostan-6-one (2) (1.20 g, 21 %):

Rf 0.32 (benzene/ethyl acetate; 5:1), m.p. 199 to 201° C. (Hexane-ethyl acetate), ¹H-NMR (CDCl₃) δ 0.67 (3H, s, 18-H₃), 0.98 (3H, s, 19-H₃), 1.99 (3H, s, acetyl), 2.13 (3H, s, acetyl), 2.50 (2H, m, 22-H and 23-H), 3.00 (1H, dd, J=12 and 5 Hz, 5α-H), 4.08 (2H, m, 7-H₂), 4.86 (1H, m, 2β-H), 5.35 (1H, m, 3β-H), FD-MS m/z 547 (M⁺+1), and 2.19 g (39 %) of a mixture of (22R, 23R, 24R)2α,3α-diacetoxy-22,23-epoxy-B-homo-7--oxa-5α-ergostan-6-one (1) and (22S, 23S, 24R)-2α,3α-diacetoxy-22,23-epoxy-B-homo-7-oxa-5α--ergostan-6--one (2).

SYNTHESIS EXAMPLE 3

Synthesis of a mixture (3) of (22R, 23R, 24R)2α,3α-diacetoxy-22,23-epoxy-B-homo---7-oxa-5α-ergostan-6-one (1) and (22S, 23S, 24R)2α,3α-diacetoxy-22,23-epoxy-B-7-oxa-5α-ergostan-6-one (2):

(22E, 24R)-2α,3α-diacetoxy-5α-ergost-22-en-6-one (1.0 g, 1.95 mmol) was dissolved in dichloromethane (12 ml), added with m-chloroperbenzoic acid (1.2 g), and stirred in the dark at room temperature for 12 days. Dichloromethane (30 ml) and calcium hydroxide (1.2 g) were added to the reaction mixture, and after stirring at room temperature for 1 hour, filtered. The solvent was removed with an evaporator to give a crude product. It was purified by means of silica-gel column chromatography to give a mixture (3) (775 mg, 73%) of (22R, 23R)2α,3α-diacetoxy-B-homo-7-oxa-5α-ergostan-6-one (1) and (22S, 23S)2α,3α-diacetoxy-B-homo-7-oxa-5α-ergostan-6-one (2).

Rf 0.36 and 0.32 (benzene/ethyl acetate, 5:1),

¹H NMR (CDCl₃) δ 0.66 (3H, s, 18-H₃), 0.99 (3H, s, 19-H₃), 1.99 (3H, s, acetyl), 2.12 (3H, s, acetyl), 2.20 to 2.70 (2H, m, 22-H and 23-H), 3.00 (1H, dd, J=12 and 5 Hz, 5α-H), 4.09 (2H, m, 7-H₂), 4.85 (1H, m, 28-H), 5.36 (1H, m, 3β-H), FD-MS m/z 547 (M⁺+1).

SYNTHESIS EXAMPLE 4

Synthesis of (22R, 23R, 24S)2α,3α-diacetoxy-22,23-epoxy-B-homo-7-oxa-5α-stigmastan--6-one (11) and (22S, 23S, 24S)2α,3α-diacetoxy-22,23-epoxy-B-homo-7-oxa-5α-stigmastan-6-one (12):

(22E, 24S)2α,3α-Diacetoxy-5α-stigmast-22-en-6-one (S. Takatsuto and N. Ikekawa, Chem. Pharm. Bull., 30, 4181 (1982)) (4.48 g, 8.48 mmol) was oxidized by m-chloroperbenzoic acid in the similar manner to Example 2, and the product obtained was purified by means of silica-gel column chromatography to give (22R, 23R, 24S)2α,3α-diacetoxy-22,23-epoxy-B-homo-7-oxa-5α-stigmastan-6-one (11) (2.13 g, 45%):

Rf 0.50 (benzene/ethyl acetate, 5:1, 2 times developed), m.p. 191 to 193° C (ethyl alcohol).

¹H-NMR (CDCl₃) δ 0.67 (3H, s, 18-H₃), 0.99 (3H, s, 19-H₃), 2.00 (3H, s, acetyl), 2.13 (3H, s, acetyl), 2.70 (1H, dd, J=8 and 2Hz, 22-H), 3.01 (1H, dd, J=12 and 4.9 Hz, 5α-H), 4.10 (2H, m, 7-H2), 4.87 (1H, m, 2β-H), 5.37 (1H, m, 3β-H), FD-MS m/z 561 (M⁺+1) and (22S, 23S, 24S)-2α,3α-diacetoxy-22,23-epoxy-B-homo-7-oxa-5α-stigmastan-6-one (12) (1.28 g, 27 %):

Rf 0.46 (benzene/ethyl acetate, 5:1, 2 times developed)

¹H NMR (CDCl₃) δ 0.66 (3H, s, 18-H₃), 0.99 (3H, s, 19-H₃), 2.00 (3H, s, acetyl), 2.13 (3H, s, acetyl), 2.48 (2H, m, 22-H and 23-H), 3.01 (1H, dd, J=12 and 4.9 Hz, 5α-H), 4.10 (2H, m, 7-H2), 4.87 (1H, m, 2β-H), 5.37 (1H, m, 3β-H).

FD—MS m/z 561 (M⁺+1).

SYNTHESIS EXAMPLE 5

Synthesis of a mixture (13) of (22R, 23R, 24S)2α,3α-diacetoxy-22,23-epoxy-B--homo-7-oxa-5α-stigmastan-6-one (11) and (22S, 23S, 24S)2α,3α-diacetoxy-22,23-epoxy-B-homo-7-oxa-5α-stigmastan--6-one (12):

(22E, 24S)-2α,3α-Diacetoxy-5α-stigmast-22-en-6-one (2.50 g, 4.73 mmol) was oxidized with m-chloro perbenzoic acid in the similar manner to Example 2, and the obtained product was purified by means of silica-gel column chromatography to give a mixture (1.88 g, 71 %) (13) of (22R, 23R, 24S)-2α,3α-diacetoxy-22,23-epoxy-B-homo-7-oxa-5α-stigmastan-6-one (11) and (22S, 23S, 24S)2α,3α-diacetoxy-22,23-epoxy-B-homo-7-oxa-5u-stigmastan-6--one (12).

Rf 0.50 and 0.46 (benzene/ethyl acetate, 5:1, 2 times developed)

m.p. 177° to 183° C. (ethyl alcohol).

SYNTHESIS EXAMPLE 6

Synthesis of a mixture (13) of (22R, 23R, 24S)2α,3α-diacetoxy-22,23-epoxy-B-homo---7-oxa-5α-stigmastan-6-one (11) and (22S, 23S, 24S)2α,3α-diacetoxy-22,23-epoxy-B-homo-7-oxa-5α---stigmastan-6-one (12):

A mixture (500 mg, 0.919 mmol) of (22R, 23R)2α,3α-diacetoxy-22,23-epoxy-5α---stigmastan-6-one and (22S, 23S) 2α,3α-diacetoxy-22,23-epoxy-5α-stigmastan-6-one (M. Sakakibara and K. Mori, Agric. Biol. Chem., 46, 2769 (1982)) was dissolved in dichloromethane (7 ml), added with m-chloroperbenzoic acid (600 mg), and stirred in the dark at room temperature for 11 days. Dichloromethane (20 ml) and calcium hydroxide (600 mg) were added thereto, and after stirring at room temperature for 1 hour was filtered, and solvents were removed with an evaporator to give a crude product. It was purified by means of silica-gel column chromatography (2.0 cmφ×30 cm, benzene/ethyl acetate, 20:1→5:1) to give a mixture (13) (376 mg, 73%) of (22R, 23R, 24S)2α,3α-diacetoxy-22,23-epoxy-B-homo---7-oxa-5α-stigmastan-6-one (11) and (22S, 23S, 24S)-2β,3u-diacetoxy-22,23-epoxy-B-homo-7-oxa-5u-stigmastan--6-one (12).

Rf 0.50 and 0.46 (benzene/ethyl acetate, 5:1, 2 times developed)

m.p. 176° to 182° C. (ethyl alcohol).

SYNTHESIS EXAMPLE 7

Synthesis of (22E, 24S)2α,3α-diacetoxy-5α-ergost-22-6-one:

(22E, 24S)-5α-Ergosta-2,22-dien-6-one (M. Anastasia et al. J. Chem. Soc., Perkin Trans. 1, 383, 1983) (300 mg, 0.758 mmol) was oxidized with osmium tetraoxide in the similar manner to Example 1, and then acetylated. The obtained product was purified by means of silica-gel column chromatogaphy to give (22E, 24S)2α,3α-diacetoxy-5α-ergost-22-en-6-one (280 mg, 72 %);

Rf 0.39 (benzene/ethyl acetate, 10:1)
m.p. 199° to 201° C. (ethyl alcohol)
$^1$H-NMR (CDCl ) 6 0.68 (3H, s, 18-H ), 0.81 (3H, d, J=6.6 Hz, 28-H$_3$), 0.83 (3H, s, 19-H$_3$), 0.83 (3H, d, J=6.8 Hz, 26-H$_3$), 0.91 (3H, d, J=6.8 Hz, 27-H$_3$), 1.01 (3H, d, J=6.6 Hz, 21-H$_3$), 2.00 (3H, s, acetyl), 2.09(3H, s, acetyl), 2.58 (1H, dd, J=11.3 and 6.3 Hz, 5α-H), 4.95 (1H, m, 28-H), 5.16 (2H, m, 22-H and 23-H), 5.38 (1H, m, 3β-H).
EI—MS m/z 514 (M+).

SYNTHESIS EXAMPLE 8

Synthesis of (22R, 23R, 24S)-2α,3α-diacetoxy-22,23-epoxy-B-homo-7-oxa-5α-ergostan--6-one (6) and (22S, 23S, 24S)-2α,3α-diacetoxy-22,23-epoxy-B-homo-7--oxa-5α-ergostan-6-one (7):

(22E, 24S)2α,3α-Diacetoxy-5α-ergost-22-en-6-one (250 mg, 0.486 mmol) was oxidized with m-chloro perbenzoic acid in the similar manner to Example 2, and the obtained product was purified by means of silica-gel column chromatography to give a mixture (8) (188 mg, 71 %) of (22R, 23R, 24S)-2α,3α-diacetoxy-22,23-epoxy-B-homo-7-oxa-5α-ergostan-6-one (6) and (22S, 23S, 24S)-2α,3α-diacetoxy-22,23-epoxy-B-homo-7-oxa-5α-ergostan--6-one (7).

Rf 0.48 and 0.44 (benzene/ethyl acetate, 5:1, 2 times developed)
m.p. 200° to 205° C. (ethyl acetate).
$^1$H-NMR(CDCl$_3$) δ 0.67 (3H, s, 18-H$_3$), 0.99 (3H, s, 19-H$_3$),
1.99 (3H, s, acetyl), 2.13 (3H, s, acetyl),
2.21–2.75 (2H, m, 22-H and 23-H), 3.00 (1H, dd, J=12 and 5Hz, 5α-H), 4.09 (2H, m, 7-H$_2$), 4.87 (1H, m, 2β-H), 5.37 (1H, m, 3β-H).
FD-MS m/z 547 (M+ + 1)

Further, 100 mg of the above mixture were separated by means of semi-preparative thin layer chromatography (benzene/ethyl acetate, 5:1, 2 times developed) to give (22R, 23R, 24S)-2α,3α-diacetoxy-22,23-epoxy-B-homo-7-oxa-5α-ergostan-6-one (6) (64 mg):

Rf 0.48 (benzene/ethyl acetate, 5:1, 2 times developed).
$^1$H-NMR(CDCl$_3$) δ 0.67 (3H, s, 18-H$_3$), 0.99 (3H, s, 19-H$_3$), 2.00 (3H, s, acetyl), 2.12 (3H, s, acetyl), 2.55 (1H, dd, J=6.6 and 2.2 Hz, 22-H), 2.72 (1H, dd, J=6.3 and 2.2 Hz, 23-H), 3.01 (1H, dd, J=12.0 and 4.9 Hz, 5α-H), 4.10 (2H, m, 7-H$_2$), 4.87 (1H, m, 28-H), 5.37 (1H, m, 3β-H),
and (22S, 23S, 24S)-2α,3α-diacetoxy-22,23-epoxy-B-homo-oxa-5α-ergostan-6-one (7) (32 mg):

Rf =0.44 (benzene/ethyl acetate, 5:1, 2 times
$^1$H-NMR(CDCl$_3$) δ 0.67 (3H, s, 18 H$_3$), 0.99 (3H, s, 19-H$_3$),
2.00 (3H, s, acetyl), 2.13 (3H, s, acetyl),
2.46 (2H, m, 22-H and 23-H), 3.01 (1H, dd, J=12.0 and 4.9 Hz, 5α-H), 4.09 (2H, m, 7-H$_2$), 4.86 (1H, m, 2β-H), 5.37 (1H, m, 3β-H).

SYNTHESIS EXAMPLE 9

Synthesis of (22E, 24R)2α,3α-isopropylidenedioxy-5α-ergost-22-en-6-one:

50 ml of 5% solution of potassium hydroxide in methanol were added to (22E, 24R)-2α,3α-diacetoxy-5α-ergost-22-en-6-one (3.50 mg, 6.81 mmol), and heated under reflux for 30 minutes. After cooling, 100 ml of water were added thereto and extracted with dichloromethane. The obtained organic layer was washed with a saturated brine, and dried over anhydrous magnesium sulfate. Then the solvent was removed with an evaporator to give a crude product. This was dissolved in 100 ml of 2,2-dimethoxypropane, and 100 mg of p-toluenesulfonic acid were added thereto and heated under reflux for 2 hours. After cooling, the reaction mixture was extracted with ethyl acetate, and the obtained organic layer was washed with a saturated solution of sodium hydrogen carbonate, and dried over anhydrous magnesium sulfate. The solvent was removed with an evaporator to give a crude product, which was purified by means of silica-gel column chromatography (3 cmφ×34 cm. benzene/ethyl acetate, 20:1) to give (22E, 24R)-2α,3α-isopropylidenedioxy-5α-ergost-22-en-6-one (2.75 g, 86%):

Rf 0.42 (benzene/ethyl acetate, 10:1)
m.p. 161° to 163° C. (ethyl alcohol).
$^1$H-NMR(CDCl$_3$) δ 0.66 (3H, s, 18-H$_3$), 0.67 (3H, s, 19-H$_3$),
1.34 (3H, s, acetonide), 1.50 (3H, s, acetonide),
2.54 (1H, dd, J=12.0 and 4.4 Hz, 5α-H),
4.10 (1H, m, 2β-H), 4.28 (1H, m, 3β-H),
5.18 (2H, m, 22-H and 22-H and 23-H).
EI-MS m/z 470 (M+).

SYNTHESIS EXAMPLE 10

Synthesis of (22R, 23R, 24R)-22,23-epoxy2α,3α-iso-propylidenedioxy-B-homo--7-oxa--5α-ergostan-6-one (24):

(22E, 24R)-22,23-isopropylidenedioxy-5α-ergost-22-en-6-one (2.50 mg, 5.32 mmol) was oxidized with m-chloroperbenzoic acid in the similar manner to Example 2, and the product was purified by means of silica-gel column chromatography (2.5 cmφ×40 cm, hexane/ethyl acetate 4:1) to give (22R, 23R, 24R)-22,23-epoxy2α,3α-isopropylidenedioxy-B-homo-7-oxa-5α-ergostan-6-one (24)(0.96 g, 36%):

Rf 0.27 (hexane/ethyl acetate, 4:1, 3 times developed).
$^1$H-NMR (CDCl$_3$) δ 0.70 (3H, s, 18-H$_3$), 0.89 (3H, s, 19-H$_3$)
1.32 (3H, s, acetonide), 1.53 (3H, s, acetonide), 2.30 to 2.60 (2H, m, 4α-H and 23-H), 2.68 (1H, dd, J=7.1 and 2.2 Hz, 22-H), 3.30 (1H, dd, J=10 and 4.5 Hz, 5α-H), 4.11 (2H, m, 7-H$_2$), 4.38 (2H, m, 2-H and 3-H), EI-MS m/z 502 (M+).

SYNTHESIS EXAMPLE 11

Synthesis of (22R, 23R, 24R)2α,3α-dihydroxy-22,23-epoxy-B-homo-7-oxa-5α--ergostan-6-one (4):

(22E, 24R)-5α-Ergosta-2,22-dien-6-one (2.0 g, 5.1 mmol) was oxidized with osmium tetraoxide in the similar manner to Example 1, and purified by recrystallization from ethyl acetate. The obtained product was oxidized with mchloroperbenzoic acid subsequently in the similar manner to Example 2, and the product was purified by means of silicagel column chromatography to give (22R, 23R, 24R)2α,3α-dihydroxy-22,23-epoxi-B-homo--7-oxa-5α-ergostan-6-one (4) (0.49 g, 21%):

Rf 0.36 (benzene/ethyl acetate, 2:1)

$^1$H-NMR (CDCl$_3$) δ 0.67 (3H, s, 18H$_3$), 0.98 (3H, s, 19 H$_3$), 2.71 (1H, m, 22-H), 3.00 (1H, dd, J=12 and 5 Hz, 5α-H), 3.73 (1H, m, 28-H), 4.10 (3H, m, 3β-H and 7-H$_2$).

FD-MS m/z 463 (M$^+$+1)

Formulation Examples of the present invention will be illustrated below. Wherein the kind and mixing proportion of adjuvants are not limited thereby, but may be used under wider range. The word "part" in examples means part by weight.

FORMULATION EXAMPLE 1:

DUST 0.001 part of Compound No. 1 was mixed with 20 parts of talc and 79.999 parts of clay and pulverized to give a dust.

FORMULATION EXAMPLE 2:

WETTABLE POWDER 0.1 part of Compound No. 2 was mixed with 94.9 parts of kaolin, 3 parts of higher alcohol sodium sulfate and 2 parts of sodium ligninsulfonate and pulverized to give a wettable powder

FORMULATION EXAMPLE 3:

GRANULES 0.001 part of Compound No. 3 was mixed with 36 parts of diatomaceous earth, 24 parts of bentonite, 37.999 parts of talc and 2 parts of a disintegration agent, and then moistened homogenously by adding 18 parts of water. The mixture was extruded through an injection molding machine to granulate, and after regulating granules dried to granules having a diameter of 0.6 to 1 mm.

FORMULATION EXAMPLE 4:

MICROGRANULES 0.0001 part of Compound No. 11 was mixed with 1 part of polyvinyl alcohol and 14 parts of clay homogeneously and pulverized to thick powdery matter. Speparately, 84.9 parts of coarse powders of non-oilabsorptive mineral material was charged in an appropriate mixer, and moistened by adding 15 parts of water while rotating the mixer. The above thick powdery matter was added thereto to conduct coating and dried to microgranules.

FORMULATION EXAMPLE 5:

EMULSION CONCENTRATE 0.01 parts of Compound No. 13 was dissolved in 52 parts of xylene, and 18 parts of an alkylphenol ethyleneoxide condensate and calcium alkylbenzenesulfonate (8:2) were dissolved thereto by mixing to give an emulsion concentrate.

This concentrate was diluted by water as an emulsion when used.

It will be illustrated by Test Examples below that a compound of the present invention exhibits an excellent plant-growth regulating activity on various agricultural and horticultural crops.

TEST EXAMPLE 1

The foliage treatment effect to soybean (Glycine max) Materials and Methods

Soybean (Glycine max cv. Orihime) were sown 4 seeds per pot (16 cm diameter, 13 cm depth) in the soil (volcanic ash soil) containing fertilizer (N:P:K =13:12:10,60 kg/10a).

The soybean were cultivated in the glasshouse, and they were thinned to get 2 uniform plants per pot at the stage of developing of the simple leaf.

A the beginning of the developing of the first trifoliate leaf, each 0.1, 1, 10 ppm water solution of the compounds (added "shin-glamin" ×1000 as a surfactant) were treated to foliage with micro sprayer uniformly. After the treatment, under irrigation was done every 4 days to keep the same soil water condition of each pots.

The test was done 6 replications.

5 days after treatment the length of the first and second internode, the length of petiole of the first and second trifoliate leaf and stem length were measured. Results and Discussion The compounds of the present invention gave remarkable elongation of the first internode and the petiole of the first trifoliate leaf (Table-1). Besides the componds of the present invention gave splendid elongation of the second internode and the petiole of the second trifoliate leaf in spite that Standard A, B and C did not give the elongation of them.

The same results were obtained using each formulation prepared in Formulation Examples 1 to 5.

Standard A

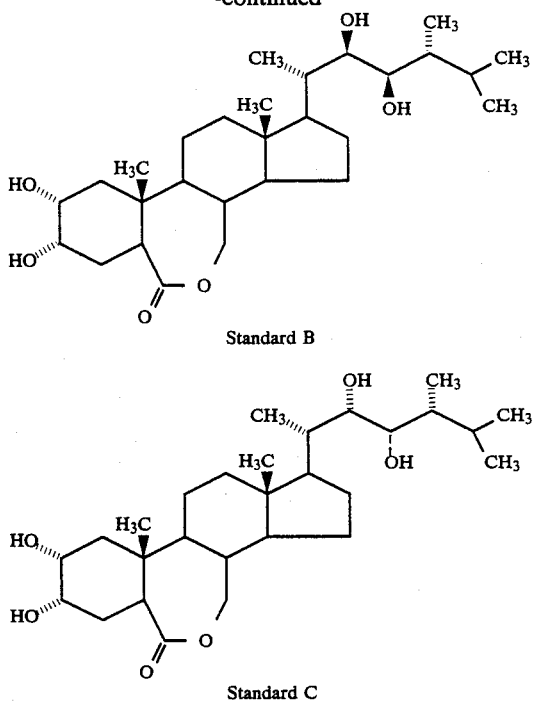

Standard B

Standard C (volcanic ash soil) containing fertilizer (N:P:K =13:12:10,60kg/10a).

The maize were cultivated in the glasshouse, and they were thinned to get 2 uniform plants per pot at the second leaf stage.

At the extract of the fourth leaf, each 0.1, 1 ppm water solution of the compounds of the present invention (added "shin-glamin" ×1000 as a surfactant) were treated to foliage with micro sprayer uniformly. After the treatment, under irrigation was done every 3 days to keep the same soil water condition of each pots.

The test was done 6 replications.

13 days after treatment the plant length and the dry weight of shoot were measured. Results and Discussion The effect of the compounds was not so clear at the point of the plant length, but the dry weight of shoot was obviously increased by the treatment of the compounds (especially, compound No. 1, No. 3, No. 11, etc.)

The same results were obtained using each formulation prepared in Formulation Examples 1 to 5.

TABLE 4

Growth-promoting effect of new compounds on corn due to foliage treatment

| Test Compound | Concentration PPM | Plant height percentage (%) per untreated | Dry weight of Shoot percentage (%) per untreated |
|---|---|---|---|
| No. 1 | 1 | 109 | 126 |
| | 0.1 | 102 | 115 |
| No. 2 | 1 | 105 | 110 |
| | 0.1 | 104 | 98 |
| No. 3 | 1 | 106 | 120 |

TABLE 3

Growth-promoting effect of new compounds on Soybean due to foliage treatment

| Test compound | Concentration PPM | First(1) internode length (%) | First(1) petiole length (%) | Second(2) internode length (%) | Second(2) petiole length (%) | Plant height (%) |
|---|---|---|---|---|---|---|
| No. 1 | 10 | 133 | 125 | 135 | 102 | 111 |
| | 1 | 136 | 131 | 168 | 119 | 117 |
| | 0.1 | 120 | 128 | 120 | 108 | 101 |
| No. 2 | 10 | 123 | 129 | 139 | 114 | 115 |
| | 1 | 121 | 129 | 129 | 110 | 110 |
| | 0.1 | 144 | 118 | 100 | 107 | 105 |
| No. 3 | 10 | 131 | 129 | 135 | 107 | 111 |
| | 1 | 128 | 138 | 176 | 132 | 118 |
| | 0.1 | 133 | 126 | 140 | 114 | 116 |
| No. 11 | 10 | 121 | 132 | 129 | 120 | 109 |
| | 1 | 129 | 126 | 136 | 116 | 111 |
| | 0.1 | 115 | 132 | 152 | 124 | 112 |
| No. 13 | 10 | 111 | 123 | 100 | 107 | 104 |
| | 1 | 113 | 120 | 124 | 110 | 106 |
| | 0.1 | 119 | 126 | 129 | 116 | 108 |
| No. 23 | 10 | 146 | 134 | 73 | 75 | 104 |
| | 1 | 136 | 138 | 96 | 81 | 107 |
| | 0.1 | 124 | 132 | 113 | 96 | 105 |
| No. 26 | 10 | 154 | 133 | 71 | 58 | 113 |
| | 1 | 120 | 117 | 84 | 70 | 99 |
| | 0.1 | 113 | 124 | 108 | 78 | 105 |
| Standard A | 10 | 114 | 126 | 70 | 65 | 97 |
| | 1 | 117 | 126 | 92 | 86 | 100 |
| | 0.1 | 128 | 125 | 113 | 98 | 100 |
| Standard B | 10 | 154 | 133 | 71 | 58 | 113 |
| | 1 | 120 | 117 | 84 | 70 | 99 |
| | 0.1 | 113 | 124 | 108 | 78 | 105 |
| Standard C | 10 | 114 | 126 | 70 | 65 | 97 |
| | 1 | 117 | 126 | 92 | 86 | 100 |
| | 0.1 | 128 | 125 | 113 | 98 | 104 |
| Untreated (water) | | 100 | 100 | 100 | 100 | 100 |

(1)The first internode shows the node between the node of first simple leaf and the node of first trifoliate leaf.
(2)The second internode shows the node between the node of first trifoliate leaf and second trifoliate leaf.
(3)(%): percentage per untreated (water)

TEST EXAMPLE 2

The foliage treatment effect to maize (Zea mays)

Materials and Methods

Maize (Zea mays cv. Honeybantam) were sown 4 seeds per pot (18 cm diameter, 14.5 cm depth) in the soil

TABLE 4-continued

Growth-promoting effect of new compounds on corn due to foliage treatment

| Test Compound | Concentration PPM | Plant height percentage (%) per untreated | Dry weight of Shoot percentage (%) per untreated |
|---|---|---|---|
| No. 8 | 0.1 | 99 | 113 |
|  | 1 | 100 | 112 |
| No. 11 | 0.1 | 105 | 98 |
|  | 1 | 108 | 123 |
| No. 13 | 0.1 | 100 | 118 |
|  | 1 | 110 | 106 |
| No. 26 | 0.1 | 97 | 115 |
|  | 1 | 104 | 104 |
| Standard A | 0.1 | 100 | 102 |
|  | 1 | 102 | 90 |
|  | 0.1 | 104 | 94 |
| Standard B | 1 | 104 | 104 |
|  | 10 | 100 | 102 |
| Standard C | 1 | 107 | 102 |
|  | 10 | 106 | 100 |
| Untreated (water) |  | 100 | 100 |

TEST EXAMPLE 3

Effect on Rice Seed Dipping Treatment Materials and Methods

A given amount of rice (Variety : Daichu 50) were dipped into the diluted solution of test compounds which were adjusted to each concentration for 14 days under the condition of 5° C.

After that, treated seeds was washed in water, sown into the pots which packed a given amount of soil and cultivated for 22 days in greenhouse. Plant height and weight of rice were measured on 25th day after seeding. Replication on this trial was carried out 4 times.

Treated date: Apr. 27, 1988
Seeded date: May 11, 1988

RESULTS AND DISCUSSION

As shown in Table-3, $10^{-5}$ PPM to $10^{-1}$ PPM of compound No. 1 increased more 23% to 77% fresh weight than the untreated, and $10^{-3}$ PPM of compound No. 2 increased 77%.

But standard B didn't almost increase fresh weight in comparison with the untreated.

The same results were obtained using each formulation prepared in Formulation Examples 1 to 5.

TABLE 5

Effect of new compounds on rice growth due to the seed dipping treatment

| Test compound | Concentration PPM | Growth of rice after 22 days | |
|---|---|---|---|
|  |  | Plant height* (%) | Fresh weight* (%) |
| No. 1 | $10^{-5}$ | 113 | 123 |
|  | $10^{-3}$ | 114 | 153 |
|  | $10^{-1}$ | 110 | 177 |
| No. 2 | $10^{-5}$ | 98 | 100 |
|  | $10^{-3}$ | 110 | 177 |
|  | $10^{-1}$ | 101 | 108 |
| Standard B | $10^{-5}$ | 103 | 115 |
|  | $10^{-3}$ | 100 | 108 |
|  | $10^{-1}$ | 104 | 108 |
| Untreated | — | 100 (19.0 cm) | 100 (130 mg) |

*percentage to untreated

What is claimed is:

1. A brassinosteroid derivative represented by the formula:

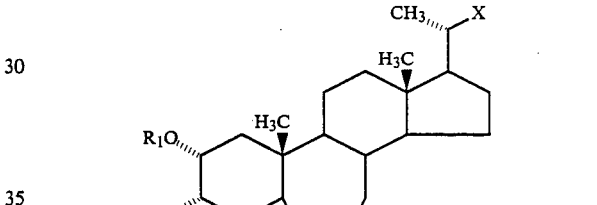

wherein
R$_3$ represents C$_{1-2}$-alkyl,
R$_1$ and r$_2$ which may be the same or different, represent hydrogen, acetyl or propionyl respectively.

2. A brassinosteroid derivative represented by the formula (I) of claim 1, wherein R$_1$ and R$_2$ are hydrogen or acetyl, R$_3$ is methyl or ethyl.

3. A brassinosteroid derivative according to claim 1 of the formula wherein R$_1$ and R$_2$ represent hydrogen or acetyl, X represent 4. A brassinosteroid derivative according to claim 2, wherien R$_1$ and R$_2$ represent acetyl and X represent

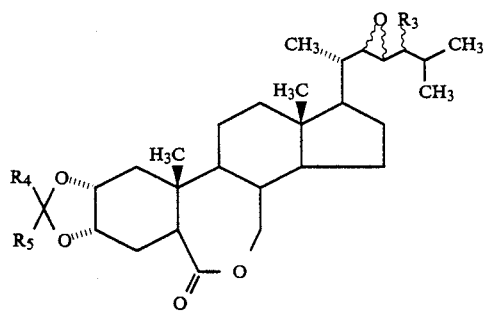
wherein $R_3$ represent methyl, $R_4$ and $R_5$ represent methyl.
5. A plant growth regulating composition comprising an effective amount of brassinosteroid represented by the formula:
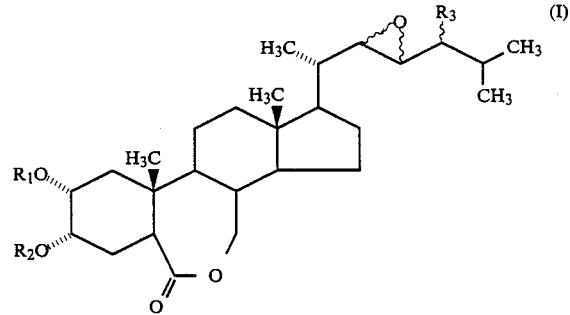
wherein $R_1$, $R_2$ and $R_3$ are as defined in claim 1, as the effective component.
* * * * *

UNITED STATES PATENT AND TRADEMARK OFFICE
CERTIFICATE OF CORRECTION

PATENT NO. : 4,961,775

DATED : October 9, 1990

INVENTOR(S) : Suguru Takatsuto, Hitoshi Sato and Fumio Futatsuya

It is certified that error appears in the above-identified patent and that said Letters Patent is hereby corrected as shown below:

Column 24, line 18, before "which may be the same" delete "$R_1$ and $r_2$" and substitute therefor --$R_1$ and $R_2$--

Column 24, line 60, after "derivative according to" delete "claim 2," and substitute therefor --claim 3,--

Column 25, delete lines 1 - 20.

Signed and Sealed this

Seventeenth Day of March, 1992

Attest:

HARRY F. MANBECK, JR.

*Attesting Officer*      *Commissioner of Patents and Trademarks*